US012760279B2

(12) United States Patent
Jeon et al.

(10) Patent No.: US 12,760,279 B2
(45) Date of Patent: Oct. 13, 2026

(54) EARLY MESENCHYMAL STEM CELLS WITH REDUCED AGING AND PRESERVED STEM CELL ABILITY, AND CULTURING METHOD THEREFOR

(71) Applicants: ENCELL CO., LTD., Seoul (KR); SAMSUNG LIFE PUBLIC WELFARE FOUNDATION, Seoul (KR)

(72) Inventors: Hong Bae Jeon, Seoul (KR); Sang Eon Park, Seongnam-si (KR); Jong Wook Chang, Seoul (KR)

(73) Assignees: ENCELL CO., LTD., Seoul (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 591 days.

(21) Appl. No.: 18/036,284

(22) PCT Filed: Nov. 9, 2021

(86) PCT No.: PCT/KR2021/016277

§ 371 (c)(1),
(2) Date: May 10, 2023

(87) PCT Pub. No.: WO2022/103129

PCT Pub. Date: May 19, 2022

(65) Prior Publication Data

US 2024/0010986 A1 Jan. 11, 2024

(30) Foreign Application Priority Data

Nov. 11, 2020 (KR) ........................ 10-2020-0150504

(51) Int. Cl.
*C12N 5/0775* (2010.01)
*A61K 35/28* (2015.01)

(52) U.S. Cl.
CPC ............ *C12N 5/0665* (2013.01); *A61K 35/28* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 7,060,494 | B2 | 6/2006 | Bhat |
| 10,047,345 | B2 | 8/2018 | Peled et al. |
| 10,947,508 | B2 | 3/2021 | Jin et al. |
| 11,332,715 | B2 | 5/2022 | Yang et al. |
| 2005/0059152 | A1 | 3/2005 | Tanavde et al. |
| 2006/0223177 | A1 | 10/2006 | Harris et al. |
| 2010/0260721 | A1 | 10/2010 | McGonagie et al. |
| 2011/0217385 | A1 | 9/2011 | Lian et al. |
| 2017/0029770 | A1 | 2/2017 | Bopardikar et al. |
| 2018/0362923 | A1 | 12/2018 | Guo |

FOREIGN PATENT DOCUMENTS

| | | | |
|---|---|---|---|
| CN | 102127522 | B | 11/2012 |
| JP | 2015-507921 | A | 3/2015 |
| JP | 2015-532596 | A | 11/2015 |
| JP | 2018-530992 | A | 10/2018 |
| KR | 10-2010-0065338 | A | 6/2010 |
| KR | 10-2013-0013435 | A | 2/2013 |
| KR | 10-2013-0057682 | A | 6/2013 |
| KR | 10-1750973 | B1 | 6/2017 |
| KR | 10-1949443 | B1 | 2/2019 |
| KR | 10-2037408 | B1 | 10/2019 |
| KR | 10-2020-0036964 | A | 4/2020 |
| KR | 10-2097191 | B1 | 4/2020 |
| WO | 2007/123363 | A1 | 11/2007 |
| WO | 2016/027850 | A1 | 2/2016 |
| WO | 2018/088821 | A1 | 5/2018 |

OTHER PUBLICATIONS

Japanese Office Action dated Sep. 2, 2025 in Application No. 2023-528328.

M.J. Peffers et al., “Age-Related Changes in Mesenchymal Stem Cells Identified Using a Multi-Omics Approach”, European Cells and Materials, 2016, vol. 31, pp. 136-159 (24 pages).

Karen Bieback, Ph.D. et al., “Altered Gene Expression in Human Adipose Stem Cells Cultured with Fetal Bovine Serum Compared to Human Supplements”, Tissue Engineering: Part A, 2010, vol. 16, No. 11, pp. 3467-3484 (19 pages).

Dolly Mushahary et al., “Isolation, Cultivation, and Characterization of Human Mesenchymal Stem Cells”, Cytometry Part A, 2018, vol. 93A, pp. 19-31 (14 pages).

Tatsanee Phermthai et al., “Successful Derivation and Characteristics of Xeno-Free Mesenchymal Stem Cell Lines from Human Amniotic Fluid Generated Under Allogenic Cord Blood Serum Supplementation”, Tissue Engineering and Regenerative Medicine, 2011, vol. No. 2, pp. 216-223 (2 pages total).

Suphakde Julavijitphong et al., “A xeno-free culture method that enhances Wharton’s jelly mesenchymal stromal cell culture efficiency over traditional animal serum-supplemented cultures”, Cytotherapy, 2014, vol. 16, pp. 683-691 (9 pages).

Ghmkin Hassan et al., “A Simple Method to Isolate and Expand Human Umbilical Cord Derived Mesenchymal Stem Cells: Using Explant Method and Umbilical Cord Blood Serum”, International Journal of Stem Cells, 2017, vol. 10, No. 2, pp. 184-192 (9 pages).

Seah Park et al., “Characterization of Umbilical Cord-derived Stem Cells during Expansion in Vitro”, Korean. J. Reprod. Med., Clinical and Experimental Reproductive Medicine, 2009, vol. 36, No. 1, pp. 23-34 (13 pages).

Wolfgang Wagner et al., “Replicative Senescence of Mesenchymal Stem Cells: A Continuous and Organized Process”, PLOS One, 2008, vol. 3, Issue 5, e2213, pp. 1-12 (12 pages).

Reza Izadpanah et al., “Long-term In vitro Expansion Alters the Biology of Adult Mesenchymal Stem Cells”, Cancer Res, 2008, vol. 68, No. 11, pp. 4229-4238 (10 pages).

(Continued)

*Primary Examiner* — Teresa E Knight
(74) *Attorney, Agent, or Firm* — Sughrue Mion, PLLC

(57) ABSTRACT

A method for culturing mesenchymal stem cells is disclosed. The method includes steps of: primary culturing mesenchymal stem cells in a medium containing umbilical cord blood serum; and subculturing the mesenchymal stem cells in a medium containing fetal bovine serum. The method for culturing mesenchymal stem cells may maintain stemness by reducing the differentiation and aging of stem cells, and in particular, may achieve a remarkably high proliferation rate.

7 Claims, 6 Drawing Sheets

(56) References Cited

OTHER PUBLICATIONS

Khushnuma Cooper et al., "Derivation, Expansion and Characterization of Clinical Grade Mesenchymal Stem Cells from Umbilical Cord Matrix Using Cord Blood Serum", International Journal of Stem Cells, 2010, vol. 3, No. 2, pp. 119-128 (11 pages).
Jooyoung Jung et al., "Mesenchymal Stromal Cells Expanded in Human Allogenic Cord Blood Serum Display Higher Self-Renewal and Enhanced Osteogenic Potential", Stem Cells and Development, vol. 18, No. 4, 2009, pp. 559-571 (13 pages).
P. Shetty, et al. "Human umbilical cord blood serum can replace fetal bovine serum in the culture of mesenchymal stem cells", Cell Biology International, vol. 31, No. 3, 2007, pp. 293-298 (6 pages).
Maryam Samareh Salavati Pour, "Cord blood serum harvesting by hydroxyethyl starch: a fetal bovine serum alternative in expansion of umbilical cord-derived mesenchymal stem cells", Cytotechnology, vol. 72, No. 4, Jun. 29, 2020, pp. 551-567 (17 pages).
Chandana Tekkatte, "Enhancement of adipogenic and osteogenic differentiation of human bone-marrow-derived mesenchymal stem cells by supplementation with umbilical cord blood serum", Cell and Tissue Research, Feb. 7, 2012, vol. 347, No. 2, pp. 383-395 (13 pages).
Extended European Search Report dated Sep. 27, 2024 in Application No. 21892296.1.

【Figure 1】
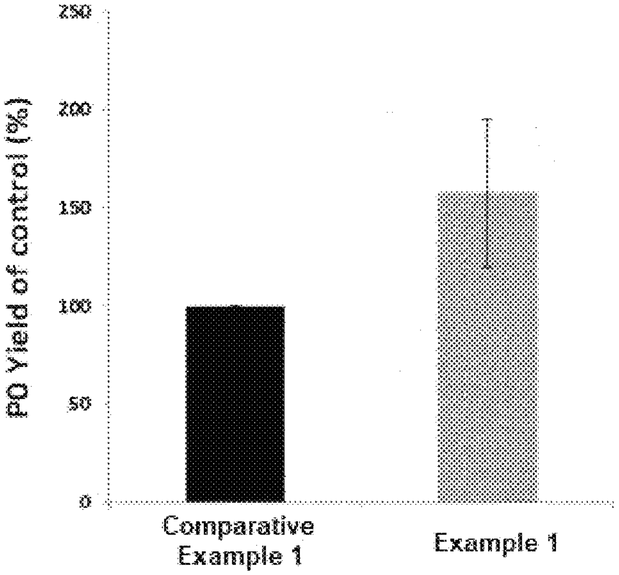
[Figure 2A]
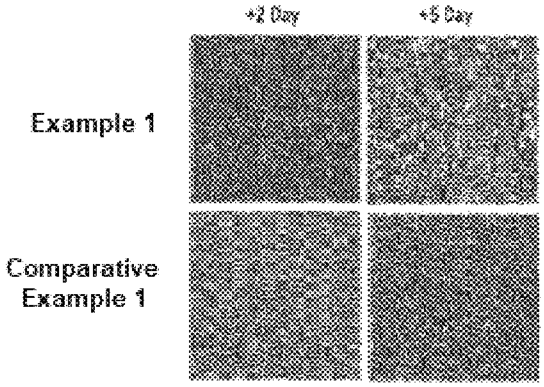
[Figure 2B]
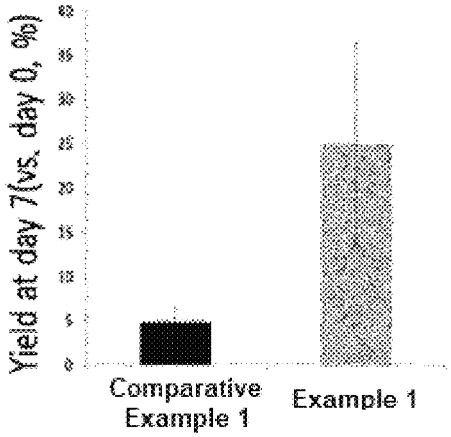

【Figure 3】
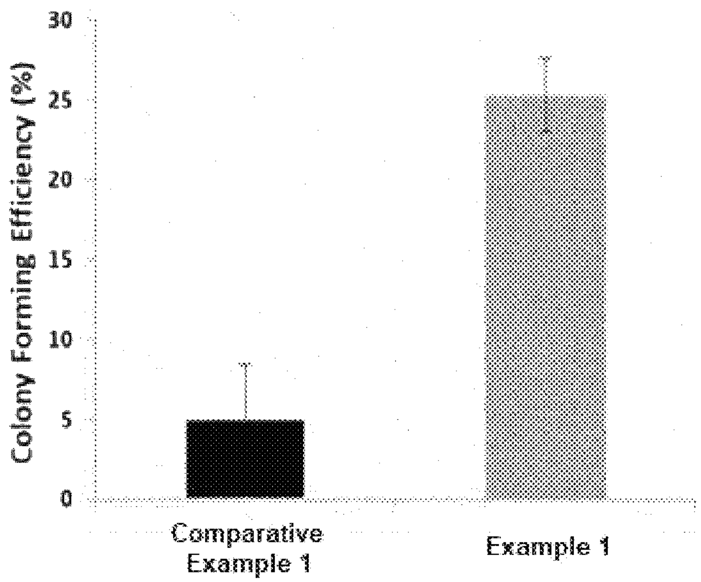
【Figure 4】
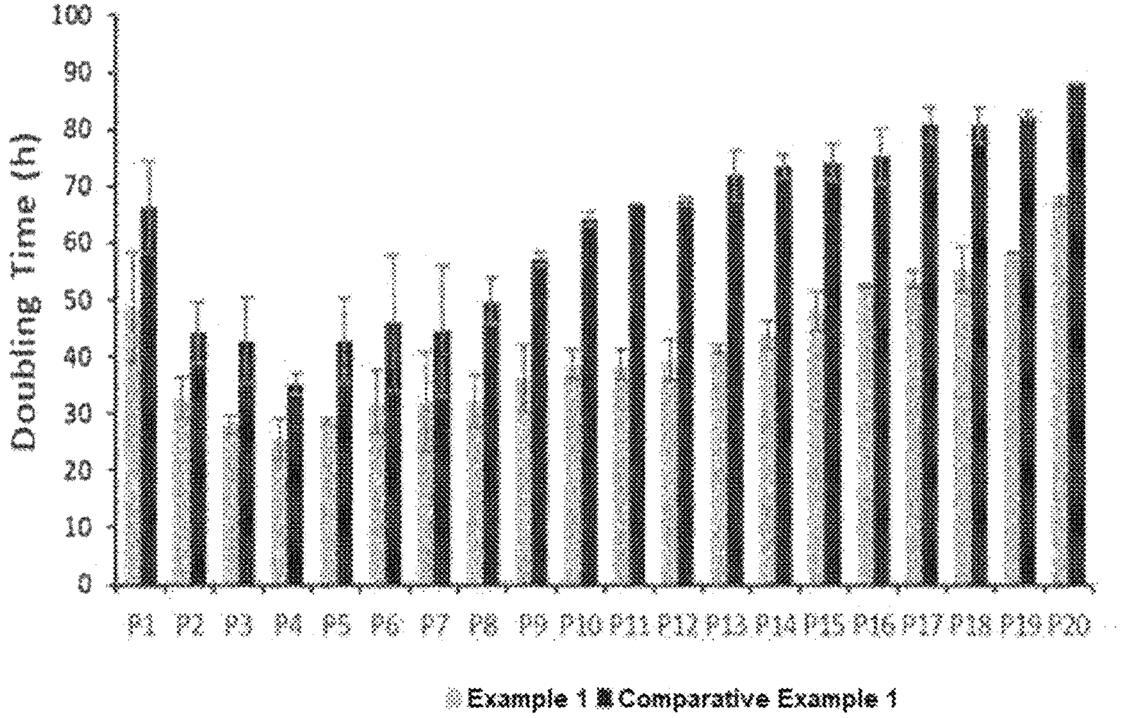

【Figure 5A】
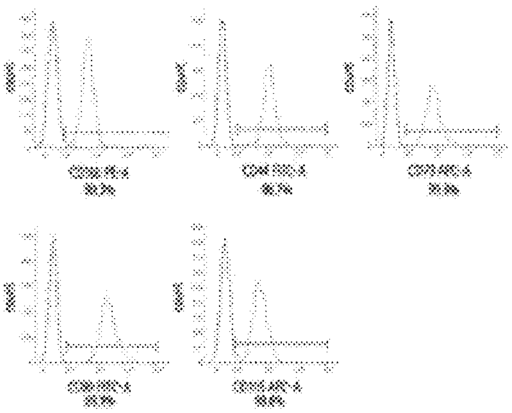
【Figure 5B】
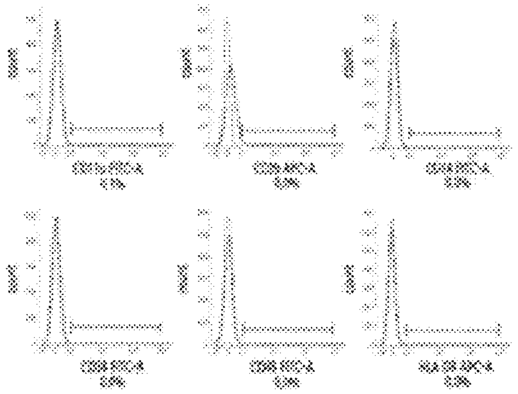
【Figure 6】
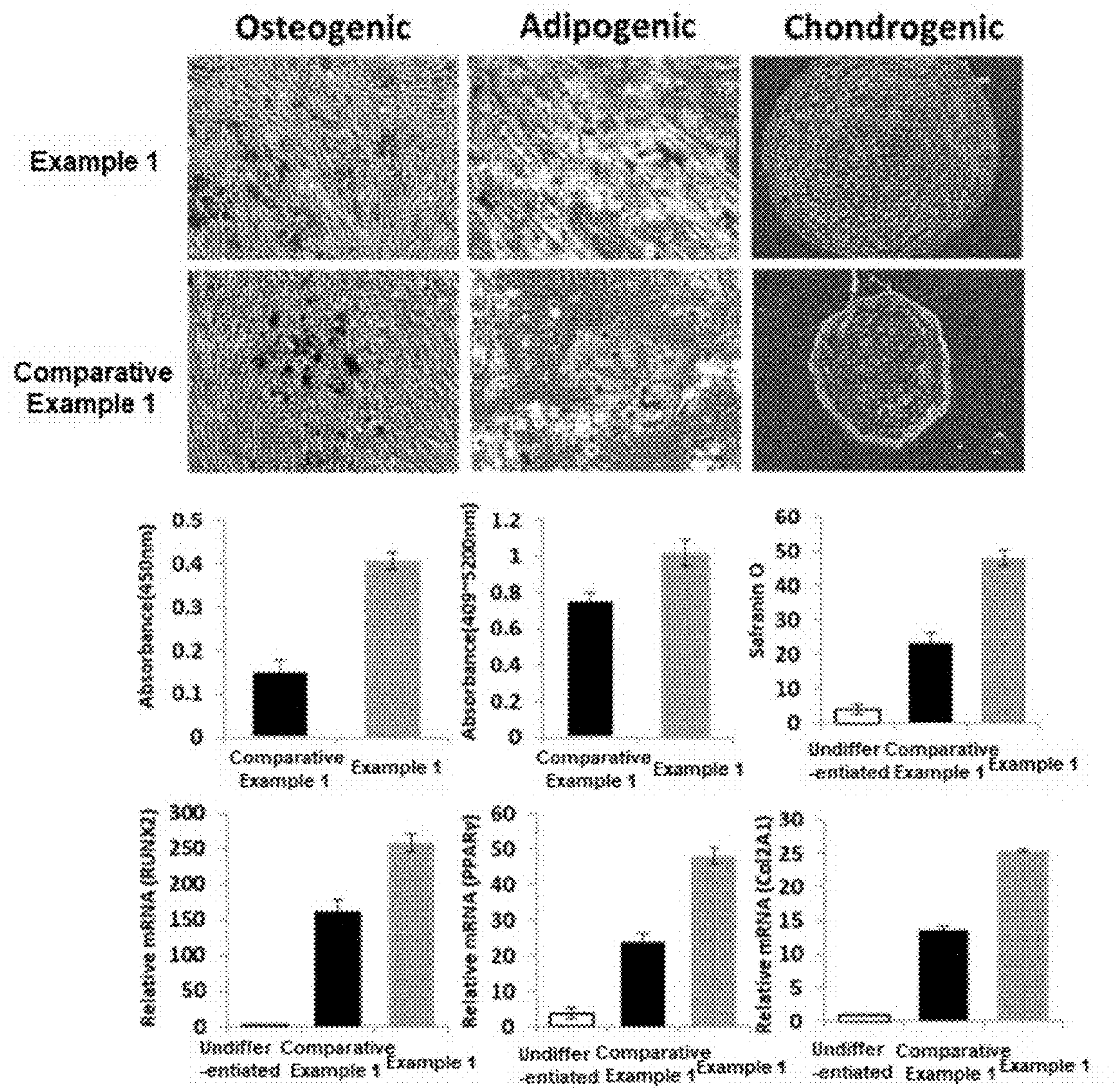

[Figure 7A]
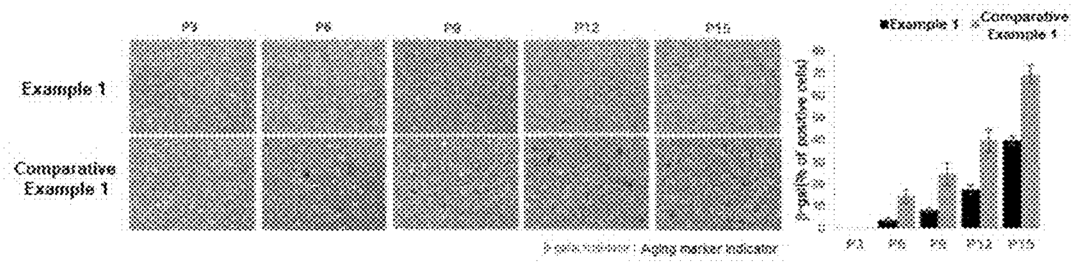
[Figure 7B]
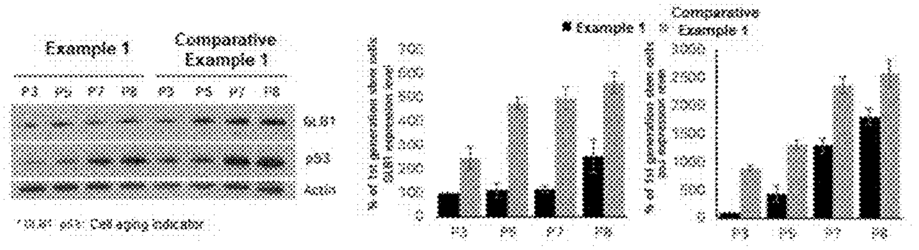

[Figure 8A]
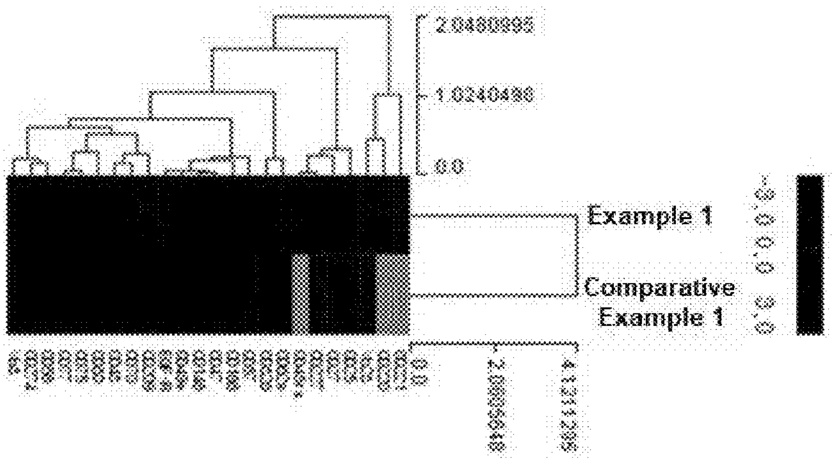
[Figure 8B]
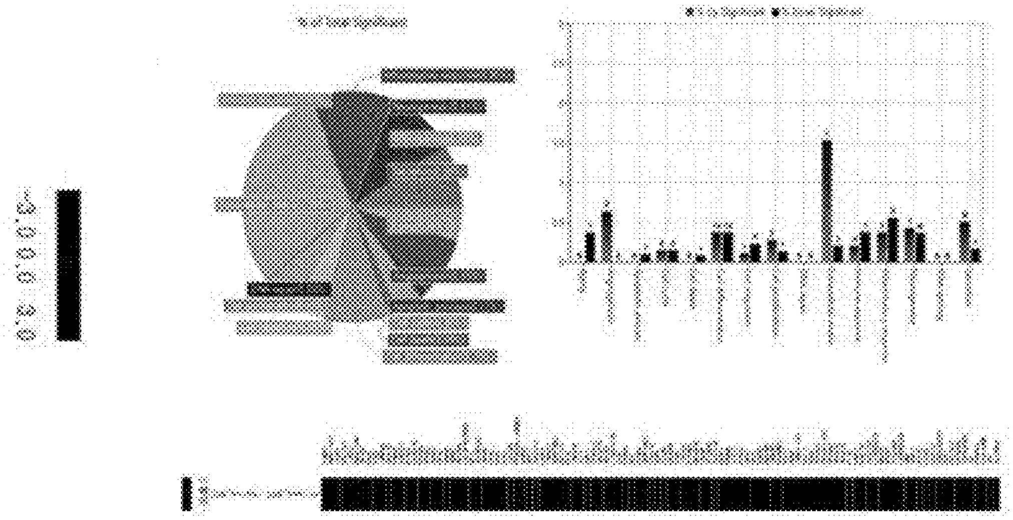

【Figure 9】
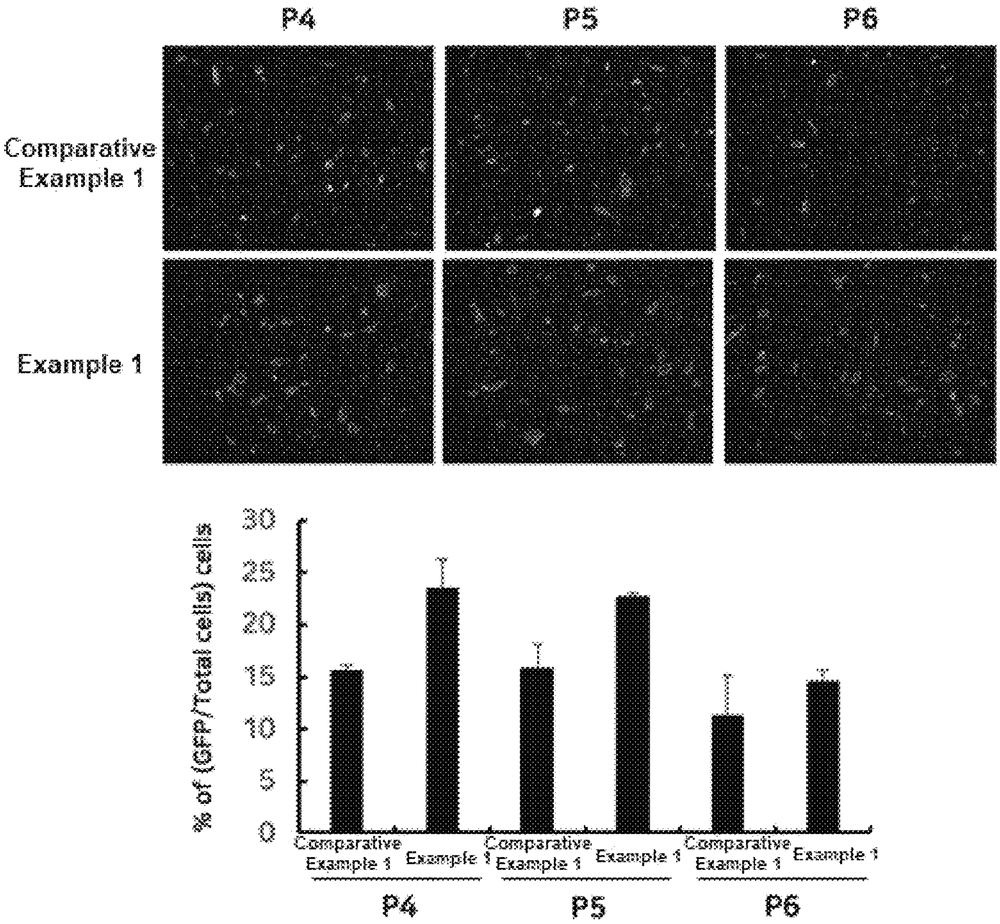

EARLY MESENCHYMAL STEM CELLS WITH REDUCED AGING AND PRESERVED STEM CELL ABILITY, AND CULTURING METHOD THEREFOR

CROSS REFERENCE TO RELATED APPLICATIONS

This application is a National Stage of International Application No. PCT/KR2021/016277 filed Nov. 9, 2021, claiming priority based on Korean Patent Application No. 10-2020-0150504 filed Nov. 11, 2020, the entire contents of which are incorporated herein as part of the present specification.

TECHNICAL FIELD

The present invention relates to an early mesenchymal stem cell with reduced aging and preserved stemness, and a method for culturing the same.

BACKGROUND ART

Stem cells can differentiate into various cells, and various studies are being conducted on the applicability of cell therapy using the characteristics of these stem cells. Embryonic stem cells with pluripotency have been attracting attention as cell therapeutic agents because of their ability to differentiate into various cells, but have difficulties in practical application due to safety and ethical issues.

In order to avoid these safety and ethical issues, many researchers have become interested in adult stem cells as an alternative to embryonic stem cells. Adult stem cells are cells that can self-renew in an undifferentiated state and multiple differentiate into various types of cells, and the first to be known are bone marrow stem cells (BMSCs) derived from bone marrow, but later it is known that they exist in various parts of our body, such as the umbilical cord, blood and fat.

Among these adult stem cells, studies using mesenchymal stem cells capable of differentiating into various tissues while having high self-replicating ability are being actively conducted.

However, since adult stem cells have a low proliferation rate, there is a problem in that the number of cells that can be obtained from one tissue is limited. In general, bone marrow-derived adult stem cells not only cause pain to the donor during their isolation process, but also are mainly used in limited cases such as bone marrow transplantation because the number of cells that can be obtained at one time is limited and the differentiation potential of the actually isolated adult stem cells is also limited.

Other types of adult stem cells, i.e., umbilical cord blood or adipose stem cells, are relatively easy to obtain, but, like bone marrow-derived adult stem cells, the number of cells that can be obtained at one time and the differentiation potential are limited.

In general, in order for stem cell therapeutic agents to be clinically applied, the number of cells more than a certain level (at least $1\times10^9$ cells) is required, and for this, mass culture of stem cells is essential. However, as the culture period of the stem cells increases, aging of the stem cells inevitably occurs, which leads to a decrease in stemness such as proliferation potential and differentiation potential, and therapeutic efficacy. In addition, since there is a disadvantage in that production costs such as material costs and labor costs increase as the culture period lengthens, the need for a method for culturing mesenchymal stem cells to proliferate them while maintaining their stemness is increasing.

PATENT DOCUMENTS

1. Korean Laid-open Patent Application No. 10-2010-0065338 (published on Jun. 16, 2010); METHOD FOR EXTRACTING MESENCHYMAL STEM CELL FROM HUMAN OR ANIMAL EMBRYO AND FOR EXTRACTING THE SECRETION PRODUCT THEREOF.
2. Chinese Patent No. CN102127522 (registered on Nov. 21, 2012); HUMAN UMBILICAL MESENCHYMAL STEM CELL AND PREPARATION METHOD THEREOF.

Non-Patent Documents

1. Seah Park, et. al., 'Analysis of Characteristic Changes of Umbilical Cord-derived Stem Cells during Expansion in Vitro,' Journal of Korean Reproductive Medicine, 2009, 36(1) 23-34.
2. Wagner et. al., 'Replicative senescence of mesenchymal stem cells: a continuous and organized process,' PLOS ONE 2008, 3, e2213.
3. Izadpanah et. al., 'Long-term in vitro expansion alters the biology of adult mesenchymal stem cells,' Cancer Research, 2008, 68, 4229-4238.

DISCLOSURE

Technical Problem

Accordingly, as a result of conducting various studies to solve the above problems, the present inventors have confirmed that a large number of mesenchymal stem cells with reduced aging while maintaining the stemness of mesenchymal stem cells may be early obtained, and have completed the present invention.

It is an object of the present invention to provide a method for culturing mesenchymal stem cells.

It is another object of the present invention to provide a method for culturing umbilical cord-derived mesenchymal stem cells after isolating them.

It is another object of the present invention to provide a method for reducing aging of mesenchymal stem cells, comprising the step of culturing mesenchymal stem cells isolated from an umbilical cord.

It is another object of the present invention to provide the isolated and cultured mesenchymal stem cells.

It is another object of the present invention to use the isolated and cultured mesenchymal stem cells as cell therapy agents for various diseases by themselves or by transformation.

Technical Solution

In order to achieve the above objects, the present invention provides a method for culturing mesenchymal stem cells.

According to an embodiment of the present invention, there is provided a method for culturing mesenchymal stem cells, comprising the steps of: primary culturing isolated human mesenchymal stem cells in a medium containing umbilical cord blood serum; and subculturing the isolated human mesenchymal stem cells in a medium containing fetal bovine serum.

The human mesenchymal stem cells are derived from bone marrow stroma, adipose tissue, umbilical cord, cartilage, placenta, or umbilical cord blood.

The umbilical cord blood serum is contained in the medium at a volume ratio of 0.5% to 30%.

The fetal bovine serum is contained in the medium at a volume ratio of 0.5% to 30%.

The subculturing is performed until the 20th passaged (P20) stem cells are obtained. According to an embodiment of the present invention, there is provided a method for reducing aging of mesenchymal stem cells, comprising the steps of: isolating mesenchymal stem cells from isolated tissue using a mixed enzyme solution of collagenase and hyaluronidase; primary culturing the isolated mesenchymal stem cells in a medium containing umbilical cord blood serum; and subculturing the mesenchymal stem cells in a medium containing fetal bovine serum.

The isolated tissue is bone marrow stroma, adipose tissue, umbilical cord, cartilage, or placenta.

The umbilical cord blood serum is contained in the medium at a volume ratio of 0.5% to 30%.

The fetal bovine serum is contained in the medium at a volume ratio of 0.5% to 30%.

The subculturing is performed until the 20th passaged stem cells are obtained.

According to an embodiment of the present invention, mesenchymal stem cells with reduced aging are provided.

The mesenchymal stem cells express one or more cell surface markers of CD47, CD49e, CD56, CD62e, CD146, CD227 and CD326, in addition to CD73, CD90, CD105, CD166 and CD44, which are mesenchymal stem cell surface markers defined by the International Society for Cellular Therapy (ISCT).

In addition, the present invention provides a cell therapeutic composition comprising the mesenchymal stem cells or a composition for preparing a cell therapeutic agent.

Advantageous Effects

Mesenchymal stem cells with reduced aging may be obtained because the method for culturing mesenchymal stem cells according to the present invention has increased cell proliferation potential and reduced aging, while maintaining the stemness of mesenchymal stem cells. In addition, the mesenchymal stem cells according to the present invention may be used as a cell therapeutic composition for various diseases or a composition for preparing a cell therapeutic agent.

BRIEF DESCRIPTION OF DRAWINGS

FIGS. 1 and 2A and 2B show the results of analyzing the isolation yield and the primary culture yield (7-day culture) according to the method for isolation of mesenchymal stem cells from tissues and the method for primary culturing the isolated mesenchymal stem cells.

FIGS. 3 and 4 show the results of analyzing the stemness and cell proliferation potential of the isolated mesenchymal stem cells during subculture, and FIGS. 5A and 5B show the results of analyzing the cell surface markers of the cultured mesenchymal stem cells.

FIG. 6 shows the results of measuring the differentiation potential of cultured mesenchymal stem cells, and FIGS. 7A and 7B show the results of measuring the degree of aging.

FIGS. 8A and 8B show the results of analyzing the expression of cell surface markers and genes of the cultured mesenchymal stem cells.

FIG. 9 shows the results of analyzing gene transfer efficiency of the cultured mesenchymal stem cells.

BEST MODE

Hereinafter, the present invention will be described in more detail.

The terms and words as used in the present specification and claims should not be construed as limited to conventional or dictionary meanings, but should be construed as the meaning and concept consistent with the technical idea of the present invention based on the principle that the inventor can appropriately define the concept of the term to describe its own invention in the best way.

The terms used in the present invention are for the purpose of describing specific embodiment only and are not intended to limit the present invention. Therefore, definitions of the present terms will have to be made based on the content throughout this specification.

Singular expressions include plural expressions unless the context clearly indicates otherwise.

Throughout the specification, when a part "comprises" or "includes" an element, it means that other elements may be further included without excluding other elements, unless otherwise stated.

As used herein, the term "stem cells" refers to cells having the ability to differentiate into two or more types of cells while having self-replicating ability, and the stem cells include all types of stem cells, such as adult stem cells, pluripotent stem cells, induced pluripotent stem cells and embryonic stem cells. The embryonic stem cells may differentiate into all kinds of cells and are useful as cell therapeutic agents, but have ethical issues for humans and safety issues that they may develop into cancer upon transplantation.

The "adult stem cells" are undifferentiated stem cells that can self-renew and differentiate into various tissue cells, such as adipocytes, osteoblasts, chondrocytes, cardiocytes, hepatocytes and neurocytes, and bone marrow-derived mesenchymal stem cells (BM-MSC) are a representative example. The bone marrow-derived mesenchymal stem cells are used not only for tissue regeneration such as heart, bone and cartilage, but also as a tool for increasing engraftment after transplantation of hematopoietic stem cells (HSCs) in clinical practice. Bone marrow is best known as a source of mesenchymal stem cells, but the number and proliferation potential of stem cells decrease as the donor's age increases, and it is painful to collect bone marrow. Accordingly, mesenchymal stem cells, which can be obtained from various tissues including umbilical cord, fat, umbilical cord blood, and the like, have recently attracted attention as a source of new cell therapeutic agents.

As used herein, the term "mesenchymal stem cells" refer to mesenchymal-derived pluripotent progenitor cells before differentiation into cells of specific organs such as bone, cartilage, fat, tendon, nerve tissue, fibroblasts and muscle cells. In the present invention, mesenchymal stem cells are contained in the composition in an undifferentiated state. The mesenchymal stem cells according to the present invention may be derived from human umbilical cord, umbilical cord blood, placenta, adipose tissue, bone marrow, tonsil, human embryonic yolk sac, umbilical cord, skin, peripheral blood, muscle, liver, nerve tissue, periosteum, fetal membrane, synovium, synovial fluid, amnion, meniscus, anterior cruciate ligament, articular chondrocytes, primary teeth, pericytes, trabecular bone, infrapatellar fat pad, spleen, thymus, and the like. Preferably, they may be derived from one or more selected from the group consisting of human umbilical cord, umbilical cord blood, placenta, fat, bone marrow, and tonsil, and are derived from human umbilical cord, umbilical cord, umbilical cord blood or adipose tissue, but their origin is not limited.

Among mesenchymal stem cells, umbilical cord blood-derived mesenchymal stem cells are known to be useful cells for homeoplastic graft because they are easy to obtain, have a high engraftment rate and low immune rejection, and are widely used in actual transplantation. However, there was a problem in that the number of donors should be two or more when an adult is transplanted with umbilical cord blood-derived mesenchymal stem cells because the amount of cells to be obtained is small.

Reflecting this, there have been attempts to increase the number of cells by culturing mesenchymal stem cells isolated from tissues.

However, since the culture of isolated mesenchymal stem cells is performed in vitro, cell proliferation through culture of mesenchymal stem cells obtained from umbilical cord blood was not actually utilized due to infection by viruses and bacteria during the culture process, cell aging through subculture, differentiation into unwanted lineages, costs for culture, and the like.

Thus, attempts have recently been made to isolate and use mesenchymal stem cells from easily obtainable tissues such as umbilical cord, placenta and fat rather than umbilical cord blood in order to secure the number of mesenchymal stem cells required for transplantation, but the culture of isolated mesenchymal stem cells is still not utilized due to the aforementioned problems, and even if cultured mesenchymal stem cells are used, only primary subculture cells may be used.

Accordingly, the present invention provides a method for culturing mesenchymal stem cells to ensure a sufficient number of isolated mesenchymal stem cells after isolating mesenchymal stem cells from tissues.

The mesenchymal stem cells are preferably derived from humans, but may also be derived from other mammal animals other than fetuses or humans. The mammal animals other than humans may be canines, felines, monkeys, cows, sheep, pigs, horses, rats, mice or guinea pigs, and their origin is not limited.

The mesenchymal stem cells according to an embodiment of the present invention include mesenchymal stem cells isolated from an umbilical cord.

The mesenchymal stem cells isolated from the umbilical cord include all stem cells isolated from the umbilical cord, wherein the umbilical cord may refer to a line connecting the mother body and the belly so that the mammalian fetus can grow in the placenta, and generally refers to a tissue composed of three blood vessels, namely two umbilical arteries and one umbilical vein, surrounded by Wharton's Jelly.

When mesenchymal stem cells are isolated from the umbilical cord, it is traditionally treated with collagenase to isolate connective tissue, but in the present invention, it was treated with collagenase and hyaluroninase at the same time. Collagenase is an enzyme that hydrolyzes collagen or gelatin, and hyaluronidase is an enzyme that hydrolyzes hyaluronic acid, and mesenchymal stem cells may be efficiently isolated by degrading connective tissue present in a high proportion in the connective tissue of the umbilical cord through treatment with these enzymes.

However, enzymes used to isolate connective tissue in the isolation of mesenchymal stem cells are not limited thereto, and enzymes commonly used for isolating cells, such as dispase and trypsin capable of degrading fibronectin, collagen, and the like, may be used.

In the process of isolating mesenchymal stem cells from the umbilical cord, the simultaneous use of collagenase and hyaluronidase showed a 1.5-fold or higher yield of mesenchymal stem cells compared to that of collagenase alone.

The method for culturing mesenchymal stem cells according to an embodiment of the present invention includes two steps of primary culture (P0) and subculture.

The "primary culture" is to isolate cells from tissue and culture them for the first time. Since mesenchymal stem cells are adherent culture cells, the nutrient medium may be exchanged in the primary culture if necessary, but the culture vessel is not exchanged. In the present invention, mesenchymal stem cells isolated from the umbilical cord are first cultured in an incubator.

"Primary yield" is the number of cells proliferated by primary culture. In the present invention, it is the number of cells when primary cultured mesenchymal stem cells isolated from the umbilical cord are primary cultured.

The "subculture" refers to proliferating and maintaining the previously cultured cells after transfer to a new culture vessel. Since the mesenchymal stem cells isolated from the umbilical cord, which are the cells of the present invention, are adherent culture cells, they are removed from the culture vessel by treatment with enzymes such as trypsin, and then transferred to a new culture vessel and subcultured.

The mesenchymal stem cells isolated from the umbilical cord are primary cultured (P0) in a culture medium containing umbilical cord blood serum (UCBS). The umbilical cord blood serum is serum of umbilical cord blood present in the umbilical cord upon delivery, and is included in the medium at a volume ratio of 0.5% to 30%, 0.5% to 20%, 0.5% to 10%, or 0.5% to 5%. In addition, the umbilical cord blood serum may be included in the culture medium at a volume ratio of 0.5%, 1%, 5%, 10%, 15%, 20%, 25%, or 30% upon primary culturing.

The primary cultured mesenchymal stem cells in a medium containing umbilical cord blood serum show a 5-fold or more primary yield after 7 days of culture compared to the primary cultured mesenchymal stem cells in a medium containing fetal bovine serum.

The medium used for the culture of mesenchymal stem cells refers to a culture medium capable of supporting the growth and survival of stem cells under in vitro culture conditions, and includes all conventional media used in the field suitable for culturing stem cells. In addition, the medium and culture conditions may be selected according to the type of cell. The medium used for culture includes, but is not necessarily limited to, DMEM (Dulbecco's Modified Eagle's Medium), MEM (Minimal essential Medium), BME (Basal Medium Eagle), RPMI1640, F-10, F-12, aMEM (a-modified Minimum Essential Media), GMEM (Glasgow's Minimal essential Medium), IMDM (Iscove's Modified Dulbecco's Medium), and the like. In the present invention, it is based on aMEM used for cell culture in the art.

Additionally, it is preferable to use antibiotics and antifungal agents to prevent infection by bacteria, fungi, and the like, and substances commonly used in the art to prevent the growth of mycoplasma causing contamination. All antibiotics commonly used for cell culture, such as penicillin-streptomycin, may be used as antibiotics, and it is preferable to use commonly used substances, such as alphorericin B as an antifungal agent, and gentamicin, ciprofloxacin, azithromycin or the like as a mycoplasma inhibitor.

The primary cultured mesenchymal stem cells were subcultured using a medium containing fetal bovine serum at a volume ratio of 0.5% to 30%, 0.5% to 30%, 0.5% to 20%, 0.5% to 10%, and 0.5% to 5% until the desired cell number is obtained. In addition, the fetal bovine serum may be included in the culture medium at a volume ratio of 0.5%, 1%, 5%, 10%, 15%, 20%, 25% or 30% upon subculture. As in the primary culture medium, antibiotics and antifungal agents may be further included to prevent contamination.

Despite the small number of mesenchymal stem cells that may be previously obtained from tissues, one of the reasons why cell culture cannot be performed is cell aging through subculture.

It is known that human bone marrow-derived mesenchymal stem cells, like general somatic cells, show characteristic changes such as a decrease in proliferation rate and a decrease in differentiation potential as the number of subcultures increases during in vitro culture. In addition, in the latter part of subculture, it has been reported that the mean telomere restriction fragment (mTRF) length decreased, the number of cells stained with senescence-associated β-galactosidase (SA β-gal) increased, and the expression of genes and proteins related to the growth and proliferation of cells and the cell cycle was altered. In addition, it has been reported that when the mesenchymal stem cells isolated from the umbilical cord were subcultured and proliferated in a medium containing fetal bovine serum, partial morphological changes began to appear from the p7 passage, and almost all cells had a broad and flattened shape at p10. In addition, it has been reported that the number of cell divisions slows down as the number of subcultures increases.

However, the present invention relates to a method for culturing mesenchymal stem cells, comprising the steps of: primary culturing mesenchymal stem cells in a medium containing umbilical cord blood serum; and subculturing the mesenchymal stem cells in a medium containing fetal bovine serum, and is characterized by primary culturing in a medium containing umbilical cord blood serum followed by replacement with a medium containing fetal bovine serum in the next subculture step, unlike conventional culturing using fetal bovine serum.

The primary cultured mesenchymal stem cells in a medium containing umbilical cord blood not only showed higher stemness compared to the primary cultured mesenchymal stem cells in a medium containing fetal bovine serum, but also showed a shorter cell doubling time by 10 hours or more on average for each subculture, and increased differentiation potential into mesenchymal cells (adipocyte differentiation, osteoblast differentiation, and chondrocyte differentiation) compared to the primary cultured mesenchymal stem cells in a medium containing fetal bovine serum.

Additionally, the primary cultured mesenchymal stem cells in a medium containing umbilical cord blood serum reduced senescence-associated β-galactosidase (SA β-gal)-positive cells, which are indicators of cell aging, and also reduced the expression of proteins GLB1 and p53, which are other cell aging markers, compared to the primary cultured mesenchymal stem cells in a medium containing fetal bovine serum.

The cultured mesenchymal stem cells according to an embodiment of the present invention not only expressed CD73, CD90, CD105, CD166 and CD44, which are mesenchymal stem cell surface markers defined by the International Society for Cellular Therapy (ISCT), but also increased the expression of one or more cell surface markers of CD27, CD47, CD49e, CD56, CD62e, CD146, CD227 and CD326 compared to the mesenchymal stem cells cultured by the conventional method.

Conventionally, it has been reported that when mesenchymal stem cells isolated from the umbilical cord were subcultured and proliferated in a medium containing fetal bovine serum, the expression of cell surface markers CD49e and CD105 decreased. However, the mesenchymal stem cells according to the present invention not only increased or maintained the expression of CD49e, which has been reported to be reduced, but also increased the expression of IQGAP2 (IQ motif containing GTPase activating protein 2), which is a gene related to cell adhesion, PTPRN (protein tyrosine phosphatase receptor type N), which is a gene related to migration, FZD8 (frizzled class receptor 8) and HGF (hepatocyte growth factor), which are related to muscle cell regeneration, STXBP5L (syntaxin binding protein 5L), which is a gene related to peripheral nerve, and the like, and also reduced the expression of genes IRF6 (interferon regulatory factor 6) and FMN2 (formin-2), which are genes related to cell aging.

The mesenchymal stem cells according to an embodiment of the present invention increased gene transfer efficiency compared to the mesenchymal stem cells subcultured and proliferated in a medium containing fetal bovine serum.

Therefore, the mesenchymal stem cells according to the present invention not only may be used as a cell therapeutic agent through differentiation into desired mesenchymal cells such as chondrocytes, but also may be used as a delivery system for cell therapy to correct the gene of a patient with a problem by directly introducing a gene of interest into the mesenchymal stem cells.

The culturing method of the present invention may be applied during primary culture or subculture of stem cells. Since the proliferation of stem cells is promoted when primary culture of the stem cells is performed in the method of the present invention, there is an advantage in that a large number of stem cells may be obtained even with a small number of subcultures.

In addition, since the mesenchymal stem cells obtained through the culturing method according to the present invention do not have immunogenicity, do not induce an immune response, reduce aging and have high differentiation potential, they may be effectively used as cell therapeutic agents for humans. Therefore, the present invention provides mesenchymal stem cells with improved proliferation potential, viability, recovery rate, and the like, as well as reduced aging, obtained by the culturing method. In addition, the present invention provides a cell therapeutic agent comprising mesenchymal stem cells themselves obtained by the culturing method or differentiated cells into desired mesenchymal cells. The cell therapeutic agent according to the present invention may be used for regeneration or protection of adipocytes, osteoblasts, chondrocytes, muscle cells, nerve cells, cardiomyocytes, hepatocytes, pancreatic islet beta-cells, vascular cells, lung cells, or the like.

In addition, since the mesenchymal stem cells according to the present invention has increased gene transfer efficiency, they may be used as a cell delivery system for cell therapy to correct the gene of a patient with a problem by directly introducing a gene of interest into the mesenchymal stem cells.

Hereinafter, preferred examples will be provided to help understanding the present invention, but the following examples are only for illustrating the present invention. It will be apparent to those skilled in the art that various changes and modifications may be made within the scope and technical spirit of the present invention, and it is obvious that such changes and modifications fall within the scope of the appended claims.

Comparative Examples 1: Isolation and Primary Culture (P0) of Umbilical Cord Tissue-Derived Mesenchymal Stem Cells Human umbilical cord and umbilical cord blood were collected with the consent of the mothers after approval from the Institutional Review Board (IRB) of Samsung Medical Center.

Umbilical cord-derived mesenchymal stem cells were isolated using the method of Peng et. al. (Brain Research Bulletin, 84 (2011) 235-243). Specifically, the umbilical cord was washed several times with phosphate buffered saline (PBS), and then cut to a length of 3 to 4 cm, and crushed finely using scissors after removing blood vessels and amnion. The crushed tissue was treated with collagenase at a temperature of 37° C. for 60 minutes to isolate cells. The enzyme reaction was stopped by treatment with fetal bovine serum (FBS), and then the enzyme reaction solution was centrifuged at 1,000 g at room temperature for 10 minutes to obtain cells.

The obtained mesenchymal stem cells were washed with serum-free a-modified minimum essential media (aMEM), and then added to aMEM containing FBS and counted to 50,000 to 100,000 cells per $cm^2$, and primary culture (P0) was performed.

In addition, after primary culture (P0), the adherent cells are floated using 0.25% trypsin when the cell confluence reaches 70-80%. The cells obtained by floating were washed with serum-free aMEM, and then the cells were added to aMEM containing FBS and counted to 3,000 to 5,000 cells per $cm^2$, and subculture (P1) was performed.

Examples 1: Isolation and Primary Culture (P0) of Umbilical Cord Tissue-Derived Mesenchymal Stem Cells Mesenchymal stem cells were obtained in the same manner as in Comparative Example 1, except that a collagenase and hyaluronidase mixture was used instead of collagenase when the mesenchymal stem cells were isolated from umbilical cord tissue.

The obtained mesenchymal stem cells were washed with serum-free a-modified minimum essential media (aMEM), and then added to aMEM containing umbilical cord blood serum (UCBS) and counted to 50,000 to 100,000 cells per $cm^2$, and primary culture (P0) was performed.

In addition, after primary culture (P0), the adherent cells are floated using trypsin when the cell confluence reaches 70-80%. The cells obtained by floating were washed with serum-free aMEM, and then the cells were added to aMEM containing FBS and counted to 3,000 to 5,000 cells per $cm^2$, and subculture (P1) was performed.

Experimental Example 1: Analysis of Isolation Yield and Primary Culture (P0) Yield of Isolated Mesenchymal Stem Cells Isolation yields of the mesenchymal stem cells obtained in Example 1 and Comparative Example 1 were analyzed. As shown in FIG. 1, the stem cell yield when a collagenase and hyaluronidase mixture was used in the isolation of mesenchymal stem cells from umbilical cord tissue was increased by 1.5-fold or more compared to the same tissue weight when collagenase alone was used.

In order to analyze the effect of umbilical cord blood serum on the primary culture of mesenchymal stem cells, the isolated mesenchymal stem cells of Example 1 were analyzed for colony formation in primary culture using FBS or UCBS (FIG. 2A) and culture yield in 7-day primary culture (FIG. 2B).

In the primary culture of mesenchymal stem cells isolated from umbilical cord tissue as shown in FIG. 2A, it could be confirmed that when UCBS was used instead of FBS, colony formation was promoted, and the yield of mesenchymal stem cells showed 5-fold or more increase after 7-day primary culture (FIG. 2B).

Experimental Example 2: Analysis of Colony-Forming Ability of Mesenchymal Stem Cells As a result of analyzing the colony-forming ability of the mesenchymal stem cells obtained by P2 subculture of the isolated mesenchymal stem cells of Example 1 and Comparative Example 1, the colony-forming ability of the mesenchymal stem cells of Example 1 showed 5-fold or more increase compared to the mesenchymal stem cells of Comparative Example 1 (FIG. 3).

Experimental Example 3: Analysis of Proliferation Potential of Mesenchymal Stem Cells As a result of analyzing the doubling time for each passage in P1 to P20 subcultures of the isolated mesenchymal stem cells of Example 1 and Comparative Example 1 using aMEM medium containing FBS, it could be confirmed that the doubling time of the mesenchymal stem cells of Example 1 (Example 1) was shortened by 10 hours or more on average compared to the mesenchymal stem cells of Comparative Example 1 (Comparative Example 1) (FIG. 4).

Experimental Example 4: Analysis of Cell Surface Markers After Subculture of Mesenchymal Stem Cells Analysis of cell surface markers was performed to confirm whether the properties of the mesenchymal stem cells were maintained even after subculture of the isolated mesenchymal stem cells of Example 1 in a medium containing FBS.

The P4 subcultured cells of Example 1 in aMEM medium containing FBS were analyzed for expression patterns of mesenchymal stem cell-specific cell surface markers (CD90, CD105, CD73, CD166, and CD44) according to the requirements of the International Society for Cellular Therapy (ISCT), and were analyzed by flow cytometry for whether negative markers (CD34, CD45, CD19, CD11b, CD14, and HLA-DR) of mesenchymal stem cells were expressed, for purity analysis.

As a result, it could be confirmed that the P4 subcultured mesenchymal stem cells isolated in Example 1 still expressed 99% or more of mesenchymal stem cell-specific cell surface markers (FIG. 5A), but did not express negative markers (FIG. 5B).

Therefore, it could be confirmed that the isolated mesenchymal stem cells of Example 1 still maintained the phenotype of the mesenchymal stem cells despite subculture.

Experimental Example 5: Measurement of Differentiation Potential of Mesenchymal Stem Cells After each of the isolated mesenchymal stem cells of Example 1 and the isolated mesenchymal stem cells of Comparative Example 1 was P4 subcultured in aMEM medium containing FBS, their differentiation potential was analyzed when each of the mesenchymal stem cells was differentiated using a differentiation medium for differentiating into representative mesenchymal cells such as adipocytes, osteoblasts, and chondrocytes.

StemPro Adipogenesis Differentiation Kit was used for adipocyte differentiation, StemPro Osteogenesis Differentiation Kit was used for osteoblast differentiation, and a medium containing BMP-6, TGFβ3, insulin-transferrin-selenium (ITS), dexamethasone, ascorbic acid, L-proline, and sodium pyruvate in DMEM medium was used for chondrocyte differentiation.

The adipocytes, osteoblasts and chondrocytes were stained with oil-red O, Alizarin red S and Safranin-O, respectively, and the results are as shown in FIG. 6.

In addition, the adipocytes, osteoblasts and chondrocytes are analyzed for gene expression levels using reverse transcription polymerase reaction (RT-PCR) techniques by PPARγ (peroxisome proliferator-activated receptor gamma), RUNX2 (runt-related transcription factor 2) and Col2A1 (collagen type II alpha 1 chain), respectively, and the results are as shown in FIG. 6.

From the results of FIG. 6, the mesenchymal stem cells of Example 1 showed 1.5-fold or more increase in differentiation potential into adipocytes, osteoblasts and chondrocytes compared to the mesenchymal stem cells of Comparative Example 1.

In addition, from the results of FIG. 6, the mesenchymal stem cells of Example 1 showed 1.5-fold or more increase in the expression of genes related to differentiation potential into adipocytes, osteoblasts and chondrocytes compared to the mesenchymal stem cells of Comparative Example 1.

Experimental Example 6: Analysis of the Degree of Aging of Mesenchymal Stem Cells In order to analyze the degree of aging of the isolated mesenchymal stem cells, the expression level of β-galactosidase known to be overexpressed or accumulated in senescent cells was analyzed while the mesenchymal stem cells of Example 1 and Comparative Example 1 were subcultured (P3, P6, P9, P15). When the mesenchymal stem cells of both Example 1 and Comparative Example 1 were subcultured for 15 or more passages, no morphological change of each cell was observed.

Specifically, an SA β-gal assay kit (cell signaling) was used, and the experiment was performed according to the manufacturer's manual. Through microscopic imaging, the number of senescent cells (β-gal positive; green) per cell group was measured and graphed, and the results are as shown in FIG. 7A.

As a result, it could be confirmed that the mesenchymal stem cells of Example 1 had remarkably fewer β-galactosidase-positive cells, which may be regarded as senescent cells on the same passage basis, compared to the mesenchymal stem cells of Comparative Example 1, and in particular, the β-galactosidase-positive cells of Comparative Example 1 at P12 and P15 were 40% or more and 70% or more, respectively, whereas those of the mesenchymal stem cells of Example 1 were less than 20% and less than 40%, respectively, and thus, the mesenchymal stem cells of Example 1 had reduced aging compared to those of Comparative Example 1 (FIG. 7A).

In addition, as a result of analyzing the actual protein amounts of β-galactosidase (GLB1) and p53 for each passage in the mesenchymal stem cells of Example 1 and Comparative Example 1 by immunoblot method, as in the analysis of β-galactosidase activity, the expression levels of GLB1 and p53 in the mesenchymal stem cells of Comparative Example 1 were increased compared to the mesenchymal stem cells of Example 1 in the same passage (FIG. 7B).

Taken together, the mesenchymal stem cells of Example 1 have reduced aging compared to the mesenchymal stem cells of Comparative Example 1.

Experimental Example 7: Expression Analysis of Cell Surface Markers and Genes of Mesenchymal Stem Cells In order to analyze the types of markers expressed on the surface of the mesenchymal stem cells of Example 1 and Comparative Example 1, 242 cell surface markers were analyzed with BD Lyoplate™ using a FACS method. As a result, it could be confirmed that the mesenchymal stem cells of Example 1 showed increased expression of surface markers related to cell adhesion (CD47, CD49e, CD56, CD62e, CD146, CD227), migration (CD47), proliferation (CD47, CD227), immune regulation (CD27, CD326), and the like, compared to the mesenchymal stem cells of Comparative Example 1 (FIG. 8A, Table 1).

In particular, it can be confirmed that the expression levels of CD227, CD326, CD27 and CD62e in the mesenchymal stem cells of Example 1 are 2-fold or higher compared to the mesenchymal stem cells of Comparative Example 1.

TABLE 1

| Surface marker | Expression rate of Example 1/Comparative Example 1 |
|---|---|
| CD27 | 3.34-fold |
| CD47 | 1.59-fold |
| CD49e | 1.51-fold |
| CD56 | 1.64-fold |
| CD62e | 2.16-fold |
| CD146 | 1.21-fold |
| CD227 | 8.43-fold |
| CD326 | 4.62-fold |

In addition, in order to analyze the gene expression patterns expressed in the mesenchymal stem cells of Example 1 and Comparative Example 1, gene expression of both cells was analyzed through QuantSeq 3'mRNA-sequence (Lexogen). As a result, it could be confirmed that the mesenchymal stem cells of Example 1 specifically increased the expression of cell adhesion (IQGAP2; IQ motif containing GTPase activating protein 2), migration (PTPRN; protein tyrosine phosphatase receptor type N), muscle cell regeneration (FZD8c; frizzled class receptor 8) and muscle cell growth factor (HGF; hepatocyte growth factor), peripheral nerve-related gene (STXBP5L; syntaxin binding protein 5L), and the like, and reduced the expression of cell aging-related genes (IRF6; interferon regulatory factor 6, and FMN2; formin-2), compared to the mesenchymal stem cells of Comparative Example 1 (FIG. 8B, Table 2).

The mesenchymal stem cells of Example 1 increased the expression of cell adhesion and migration-related genes IQGAP2 and PTPRN by 2-fold or more compared to those of Comparative Example 1, which showed a similar expression pattern to the cell surface markers analyzed previously. In addition, the mesenchymal stem cells of Example 1 showed a decrease in the expression of aging-related genes IRF6 and FMN2 compared to the mesenchymal stem cells of Comparative Example 1, and this result is consistent with the result that the mesenchymal stem cells of Example 1 in Experimental Example 6 showed a decrease in senescence compared to those of Comparative Example 1.

TABLE 2

| Gene | Expression rate of Example 1/Comparative Example 1 |
|---|---|
| IQGAP2 | 4.52-fold |
| PTPRN | 2.43-fold |
| FZD8 | 2.02-fold |
| HGF | 2.13-fold |
| STXBP5L | 3.90-fold |
| IRF6 | 0.41-fold |
| FMN2 | 0.49-fold |

Experimental Example 8: Analysis of Gene Transfer Efficiency in Mesenchymal Stem Cells In order to analyze the gene transfer efficiency of the mesenchymal stem cells of Example 1 and Comparative Example 1, the GFP expression vector encoding the GFP gene was transfected into the mesenchymal stem cells of Example 1 and Comparative Example 1 at P4, P5, and P6 passages, and transfection efficiency was calculated as cells expressing GFP protein compared to total cells.

As a result, it could be confirmed that the mesenchymal stem cells of Example 1 had higher transfection efficiency at P4 and P5 passages compared to the mesenchymal stem cells of Comparative Example 1 (FIG. 9).

Therefore, since the mesenchymal stem cells of Example 1 has increased gene transfer efficiency compared to the mesenchymal stem cells of Comparative Example 1, they may be used as a cell delivery system for cell therapy to correct the gene of a patient with a problem by directly introducing a gene of interest into the mesenchymal stem cells.

Although the present invention has been described above with reference to limited examples and drawings, the present invention is not limited thereto, and it will be apparent that various modifications and variations may be made within the scope of the technical spirit of the present invention and equivalents of the claims to be described below by those skilled in the art to which the present invention pertains.

The invention claimed is:

1. A method for culturing mesenchymal stem cells, comprising the steps of:

primary culturing isolated human mesenchymal stem cells derived from an umbilical cord in a medium containing umbilical cord blood serum; and subculturing the isolated human mesenchymal stem cells derived from the umbilical cord in a medium containing fetal bovine serum.

2. The method for culturing mesenchymal stem cells according to claim 1, wherein the umbilical cord blood serum is contained in the medium at a volume ratio of 0.5% to 30%.

3. The method for culturing mesenchymal stem cells according to claim 1, wherein the fetal bovine serum is contained in the medium at a volume ratio of 0.5% to 30%.

4. The method for culturing mesenchymal stem cells according to claim 1, wherein the subculturing is performed until the 20th passaged stem cells are obtained.

5. A method for reducing aging of mesenchymal stem cells, comprising the steps of: isolating mesenchymal stem cells from isolated tissue using a mixed enzyme solution of collagenase and hyaluronidase, wherein the isolated tissue is an umbilical cord; primary culturing the isolated mesenchymal stem cells in a medium containing umbilical cord blood serum; and subculturing the mesenchymal stem cells in a medium containing fetal bovine serum.

6. The method for reducing aging of mesenchymal stem cells according to claim 5, wherein the umbilical cord blood serum is contained in the medium at a volume ratio of 0.5% to 30%.

7. The method for reducing aging of mesenchymal stem cells according to claim 5, wherein the subculturing is performed until the 20th passaged stem cells are obtained.

* * * * *